US012655246B2

(12) United States Patent
Kawaguchi

(10) Patent No.: US 12,655,246 B2
(45) Date of Patent: *Jun. 16, 2026

(54) XYLYLENE DIISOCYANATE COMPOSITION, XYLYLENE DIISOCYANATE MODIFIED COMPOSITION, POLYMERIZABLE COMPOSITION, RESIN, MOLDED ARTICLE, OPTICAL ELEMENT, AND LENS

(71) Applicant: MITSUI CHEMICALS, INC., Tokyo (JP)

(72) Inventor: Masaru Kawaguchi, Fukuoka (JP)

(73) Assignee: MITSUI CHEMICALS, INC., Tokyo (JP)

( * ) Notice: Subject to any disclaimer, the term of this patent is extended or adjusted under 35 U.S.C. 154(b) by 209 days.

This patent is subject to a terminal disclaimer.

(21) Appl. No.: 17/778,658

(22) PCT Filed: Jun. 14, 2021

(86) PCT No.: PCT/JP2021/022484

§ 371 (c)(1),
(2) Date: May 20, 2022

(87) PCT Pub. No.: WO2022/162968

PCT Pub. Date: Aug. 4, 2022

(65) Prior Publication Data

US 2023/0340183 A1 Oct. 26, 2023

(30) Foreign Application Priority Data

Jan. 28, 2021 (JP) ................................ 2021-011959

(51) Int. Cl.

| | |
|---|---|
| ***C08G 18/76*** | (2006.01) |
| ***C07C 265/14*** | (2006.01) |
| ***C08G 18/24*** | (2006.01) |
| ***C08G 18/38*** | (2006.01) |
| ***C08G 18/71*** | (2006.01) |
| ***C08G 18/78*** | (2006.01) |
| ***C08G 18/79*** | (2006.01) |
| ***G02B 1/04*** | (2006.01) |

(52) U.S. Cl.

CPC ........ *C08G 18/7642* (2013.01); *C07C 265/14* (2013.01); *C08G 18/242* (2013.01); *C08G 18/3876* (2013.01); *C08G 18/71* (2013.01); *C08G 18/711* (2013.01); *C08G 18/7614* (2013.01); *C08G 18/78* (2013.01); *C08G 18/7831* (2013.01); *C08G 18/7837* (2013.01); *C08G 18/79* (2013.01); *C08G 18/791* (2013.01); *C08G 18/797* (2013.01); *G02B 1/04* (2013.01); *G02B 1/041* (2013.01)

(58) Field of Classification Search

CPC ............ C08G 18/7642; C08G 18/3876; C08G 18/242; C08G 18/71; C08G 18/711; C08G 18/78; C08G 18/79; C08G 18/7614; C08G 18/7831; C08G 18/7837; C08G 18/791; C08G 18/797; C07C 265/14; G02B 1/041; G02B 1/04

See application file for complete search history.

(56) References Cited

U.S. PATENT DOCUMENTS

| | | | |
|---|---|---|---|
| 2016/0046565 | A1 | 2/2016 | Takamatsu et al. |
| 2018/0334531 | A1 | 11/2018 | Shin et al. |
| 2019/0106529 | A1 | 4/2019 | Kuma |
| 2019/0292304 | A1 | 9/2019 | Yamasaki et al. |
| 2020/0102268 | A1 | 4/2020 | Park et al. |
| 2020/0190022 | A1 | 6/2020 | Lee et al. |

FOREIGN PATENT DOCUMENTS

| | | | | |
|---|---|---|---|---|
| CN | 109153637 | A | 1/2019 | |
| EP | 3309186 | A1 * | 4/2018 | ........... C08G 18/022 |
| EP | 3444236 | A1 * | 2/2019 | ......... C08G 18/3203 |
| JP | 2018193369 | A | 12/2018 | |
| JP | 2020503325 | A | 1/2020 | |
| JP | 2020024453 | A | 2/2020 | |
| JP | 2020533393 | A | 11/2020 | |
| JP | 2021091682 | A | 6/2021 | |
| WO | 2014163016 | A1 | 10/2014 | |

OTHER PUBLICATIONS

Office Action (Communication of a Notice of opposition) issued on Feb. 17, 2025, by the European Patent Office in corresponding European Application No. 21922976.2 (European Patent No. 4089071), 31 pgs.
Experimental Report cited in Office Action (Notice of opposition to a European Patent), 4 pgs.
Submission by Applicant issued on Dec. 15, 2023 by the European Patent Office in corresponding European (EP) Patent Application No. 21922976.2, 8 pgs.
TCI America, Safety Data Sheet, revised on Jul. 6, 2018 (5 pgs).
J&K Scientific XDI safety data sheet, Version 4, 9 pages.
Sigma Aldrich XDI safety data sheet, 3 pages.

* cited by examiner

*Primary Examiner* — Rabon A Sergent
(74) *Attorney, Agent, or Firm* — BUCHANAN INGERSOLL & ROONEY PC

(57) ABSTRACT

[Solving Means]
A xylylene diisocyanate composition contains a xylylene diisocyanate and a compound having retention time of 14.0 minutes to 14.6 minutes when the xylylene diisocyanate composition is measured by gas chromatography mass spectrometry under the specific measurement conditions, and a content ratio of the compound is adjusted to be 2000 ppm or less.

9 Claims, No Drawings

XYLYLENE DIISOCYANATE COMPOSITION, XYLYLENE DIISOCYANATE MODIFIED COMPOSITION, POLYMERIZABLE COMPOSITION, RESIN, MOLDED ARTICLE, OPTICAL ELEMENT, AND LENS

TECHNICAL FIELD

The present invention relates to a xylylene diisocyanate composition, a xylylene diisocyanate modified composition, a polymerizable composition, a resin, a molded article, an optical element, and a lens.

BACKGROUND ART

Conventionally, a xylylene diisocyanate composition as a raw material for a poly(thio)urethane resin used for various industrial products has been known (ref: for example, Patent Document 1).

CITATION LIST

Patent Document

Patent Document 1: Japanese Unexamined Patent Publication No. 2020-24453

SUMMARY OF THE INVENTION

Problem to be Solved by the Invention

The xylylene diisocyanate composition described in Patent Document 1 may contain a compound other than the xylylene diisocyanate in addition to the xylylene diisocyanate.

However, a resin is required to have excellent yellowing resistance and excellent transparency in accordance with its purpose and application. However, when the xylylene diisocyanate composition contains a specific compound, the yellowing resistance and the transparency of the resin produced from the xylylene diisocyanate composition may be remarkably lowered.

Accordingly, the present invention provides a xylylene diisocyanate composition, a xylylene diisocyanate modified composition, a polymerizable composition, a resin, a molded article, an optical element, and a lens capable of stably producing a resin having excellent yellowing resistance and excellent transparency.

Means for Solving the Problem

The present invention [1] includes a xylylene diisocyanate composition containing a xylylene diisocyanate and a compound having retention time of 14.0 minutes to 14.6 minutes when the xylylene diisocyanate composition is measured by gas chromatography mass spectrometry under the following measurement conditions, wherein a content ratio of the compound is 2000 ppm or less.

(Measurement Conditions for Gas Chromatography Mass Spectrometry)

- Column: HP19091L-433 HP-50+ (inner diameter of 0.25 mm×length of 30 m, film of 0.25 μm)
- Oven temperature: held at 50° C. for one minute, temperature rising from 50° C. to 280° C. at 10.0° C./min, and held for six minutes after reaching 280° C.
- Carrier gas: He 1.0 ml/min, constant flow mode
- Injection method: pulsed splitless method (150 kPa at 0.5 min)
- Injection amount: 1.0 μL
- Sample concentration: 1.0% by mass dichloromethane solution
- Injection temperature: 200° C.
- Interface temperature: 280° C.
- Quadrupole temperature: 150° C.
- Ion source temperature: 230° C.
- Detection method: Scan method (m/z: 10 to 500)

The present invention [2] includes the xylylene diisocyanate composition of the above-described [1], wherein a content ratio of the compound is above 100 ppm.

The present invention [3] includes the xylylene diisocyanate composition of the above-described [1], wherein a content ratio of the compound is 10 ppm or more.

The present invention [4] includes the xylylene diisocyanate composition of any one of the above-described [1] to [3], wherein a molecular weight of the compound is 161.

The present invention [5] includes the xylylene diisocyanate composition of any one of the above-described [1] to [4], wherein the compound is represented by the following general formula (1).

[Chemical Formula 1]

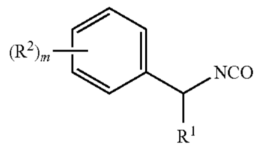

(In general formula (1), $R^1$ represents a hydrogen atom, a methyl group, or an ethyl group. $R^2$ represents a hydrogen atom, a methyl group, an ethyl group, or a formyl group. “m” represents an integer of 0 or more and 2 or less.)

The present invention [6] includes the xylylene diisocyanate composition of the above-described [5], wherein the compound includes a formyl group-containing isocyanate represented by the following chemical formula (2) and/or an ethyl group-containing isocyanate represented by the following chemical formula (3).

[Chemical Formula 2]

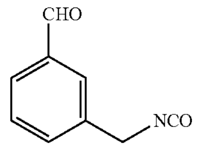

[Chemical Formula 3]

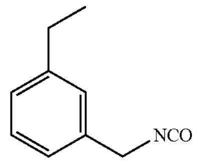

The present invention [7] includes a xylylene diisocyanate composition containing a xylylene diisocyanate and a compound represented by the following general formula (1) and having a molecular weight of 161, wherein a content ratio of the compound is 2000 ppm or less.

[Chemical Formula 1]

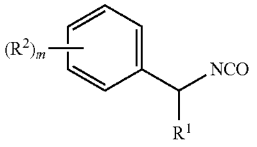

(In general formula (1), $R^1$ represents a hydrogen atom, a methyl group, or an ethyl group. $R^2$ represents a hydrogen atom, a methyl group, an ethyl group, or a formyl group. "m" represents an integer of 0 or more and 2 or less.)

The present invention [8] includes the xylylene diisocyanate composition of the above-described [7], wherein a content ratio of the compound is above 100 ppm.

The present invention [9] includes the xylylene diisocyanate composition of the above-described [7], wherein a content ratio of the compound is 10 ppm or more.

The present invention [10] includes the xylylene diisocyanate composition of any one of the above-described [7] to [9], wherein the compound includes a formyl group-containing isocyanate represented by the following chemical formula (2) and/or an ethyl group-containing isocyanate represented by the following chemical formula (3).

[Chemical Formula 2]

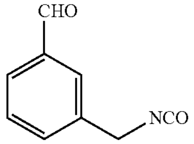

[Chemical Formula 3]

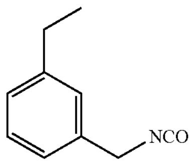

The present invention [11] includes the xylylene diisocyanate composition of any one of the above-described [1] to [10] further including a chloromethylbenzyl isocyanate, wherein a content ratio of the chloromethylbenzyl isocyanate is 0.2 ppm or more and 3000 ppm or less.

The present invention [12] includes a xylylene diisocyanate modified composition being a modified composition obtained by modifying the xylylene diisocyanate composition described in any one of the above-described [1] to [11] including at least one kind of functional groups of the following (a) to (i):

(a) isocyanurate group
(b) allophanate group
(c) biuret group
(d) urethane group
(e) urea group
(f) iminooxadiazinedione group
(g) uretdione group
(h) uretonimine group
(i) carbodiimide group The present invention [13] includes a polymerizable composition containing an isocyanate component containing the xylylene diisocyanate composition of any one of the above-described [1] to [11] and/or the xylylene diisocyanate modified composition of the above-described [12], and an active hydrogen group-containing component.

The present invention [14] includes a resin being a cured product of the polymerizable composition of the above-described [13].

The present invention [15] includes a molded article including the resin of the above-described [14].

The present invention [16] includes an optical element including the molded article of the above-described [15].

The present invention [17] includes a lens including the optical element of the above-described [16].

Effect of the Invention

The xylylene diisocyanate composition of the present invention contains the xylylene diisocyanate and the above-described compound, and the content ratio of the above-described compound is the above-described upper limit or less. Therefore, the resin produced from the above-described xylylene diisocyanate composition has excellent yellowing resistance and excellent transparency.

The xylylene diisocyanate modified composition of the present invention is obtained by modifying the above-described xylylene diisocyanate composition. Therefore, the resin produced from the above-described xylylene diisocyanate modified composition has excellent yellowing resistance and excellent transparency.

The polymerizable composition of the present invention contains, as an isocyanate component, the above-described xylylene diisocyanate composition and/or the above-described xylylene diisocyanate modified composition. Therefore, the resin produced from the above-described polymerizable composition has excellent yellowing resistance and excellent transparency.

The resin, the molded article, the optical element, and the lens of the present invention contain a cured product of the above-described polymerizable composition. Therefore, the resin, the molded article, the optical element, and the lens have excellent yellowing resistance and excellent transparency.

DESCRIPTION OF EMBODIMENTS

1. Xylylene Diisocyanate Composition

A xylylene diisocyanate composition of the present invention is a substantially single compound containing a xylylene diisocyanate at 99% by mass or more as a main component (that is, a xylylene diisocyanate). However, since it contains a specific compound to be described later (more specifically, a specific isocyanate compound) as a secondary component, it is defined as a xylylene diisocyanate composition.

In other words, the xylylene diisocyanate composition of the present invention contains the xylylene diisocyanate and the specific compound to be described later as essential components.

In the following, the xylylene diisocyanate composition is referred to as an XDI composition, and the xylylene diisocyanate is referred to as an XDI.

Examples of the XDI include 1,2-XDI (o-XDI), 1,3-XDI (m-XDI), and 1,4-XDI (p-XDI).

These XDIs may be used alone or in combination of two or more.

Of the XDIs, preferably, 1,3-XDI (m-XDI) is used.

The XDI may be produced, for example, by known hydrochloride method. Specifically, the XDI may be produced by reacting hydrochloride of xylylene diamine with phosgene under normal pressure (0.1 MPa). Also, if necessary, the XDI is refined, for example, by known refinement method. Examples of the refinement method include rectification (distillation) and extraction.

A content ratio (purity) of the XDI is, for example, 99.00% by mass or more, preferably 99.50% by mass or more, more preferably 99.60% by mass or more, further more preferably 99.80% by mass or more, and for example, 99.95% by mass or less with respect to the total mass of the XDI composition. The content ratio of the XDI may be measured in conformity with the method described in the [0377] paragraph of U.S. Pat. No. 6,373,536 in Patent Publication.

The specific compound is contained in the XDI composition, for example, by being added to the XDI. The specific compound may be also secondarily produced in the production of the above-described XDI to be contained in the XDI composition. When the specific compound is secondarily produced in the production of the XDI to be contained in the XDI composition, a method for adjusting a content ratio of the specific compound contained in the XDI composition is not limited. The content ratio of the specific compound contained in the XDI composition can be adjusted by a known method, for example, such as distillation, column refinement, and the like.

When the XDI composition is measured by gas chromatography mass spectrometry under the following measurement conditions, retention time of the specific compound is 14.0 minutes to 14.6 minutes.

(Measurement Conditions for Gas Chromatography Mass Spectrometry)

Column: HP19091L-433 HP-50+ (inner diameter of 0.25 mm×length of 30 m, film of 0.25 μm)

Oven temperature: held at 50° C. for one minute, temperature rising from 50° C. to 280° C. at 10.0° C./min, and held for six minutes after reaching 280° C.

Carrier gas: He 1.0 ml/min, constant flow mode

Injection method: pulsed splitless method (150 kPa at 0.5 min)

Injection amount: 1.0 μL

Sample concentration: 1.0% by mass dichloromethane solution

Injection temperature: 200° C.

Interface temperature: 280° C.

Quadrupole temperature: 150° C.

Ion source temperature: 230° C.

Detection method: Scan method (m/z: 10 to 500)

A molecular weight of the specific compound is 161. A specific example of the specific compound includes an isocyanate compound represented by the following general formula (1).

General Formula (1)

[Chemical Formula 1]

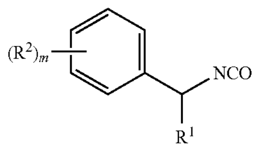

(In general formula (1), $R^1$ represents a hydrogen atom, a methyl group, or an ethyl group. $R^2$ represents a hydrogen atom, a methyl group, an ethyl group, or a formyl group. "m" represents an integer of 0 or more and 2 or less.)

In general formula (1), $R^1$ preferably represents a hydrogen atom.

In general formula (1), $R^2$ preferably represents an ethyl group or a formyl group.

In general formula (1), "m" preferably represents 1.

The isocyanate compound represented by the above-described general formula (1) preferably includes a formyl group-containing isocyanate represented by the following chemical formula (2) and/or an ethyl group-containing isocyanate represented by the following chemical formula (3), and more preferably includes the formyl group-containing isocyanate represented by the following chemical formula (2).

[Chemical Formula 2]

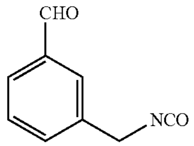

[Chemical Formula 3]

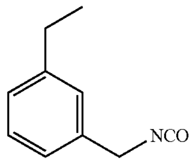

A content ratio of the specific compound is, for example, 0.1 ppm, preferably 1 ppm or more, more preferably 10 ppm or more, further more preferably above 100 ppm, and 2000 ppm or less, preferably 1700 ppm or less, more preferably 1500 ppm or less, further more preferably 1200 ppm or less, particularly preferably 1000 ppm or less with respect to the total mass of the XDI composition. The content ratio of the specific compound can be calculated in conformity with the method described in Examples to be described later. An upper limit value and a lower limit value may be appropriately used in combination.

When the content ratio of the specific compound is the above-described lower limit or more, it is possible to improve dyeability of the resin produced from the XDI composition. Further, when the content ratio of the specific compound is the above-described lower limit or more, it is possible to suppress deterioration in storage stability of the XDI composition. Further, when the content ratio of the specific compound is the above-described lower limit or more, it is possible to easily reduce the specific compound, and suppress deterioration in productivity of the XDI composition. When the content ratio of the specific compound is the above-described upper limit or less, it is possible to improve yellowing resistance and transparency of the resin produced from the XDI composition.

Further, the XDI composition may contain a chloromethylbenzyl isocyanate (monochloromethylbenzyl isocyanate) shown by the following chemical formula (4). In the following, the chloromethylbenzyl isocyanate is referred to as a CBI.

[Chemical Formula 4]

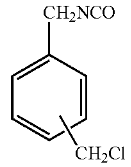

The CBI is a chlorine compound which is secondarily produced in the production of the above-described XDI. In other words, the CBI may be secondarily produced in the production of the XDI. A structural isomer of the CBI which is secondarily produced in the production of the XDI corresponds to the structural isomer of the produced XDI.

Examples of the CBI include o-CBI, m-CBI, and p-CBI.

A content ratio of the CBI is, for example, 0 ppm or more, preferably 0.2 ppm or more, preferably 6 ppm or more, more preferably 100 ppm or more, and for example, 5000 ppm or less, preferably 4000 ppm or less, more preferably 3000 ppm or less, particularly preferably 1600 ppm or less, especially preferably 1000 ppm or less with respect to the total mass of the XDI composition. The content ratio of the CBI can be measured in conformity with the method described in the paragraph [0377] of U.S. Pat. No. 6,373,536 in Patent Publication.

When the content ratio of the CBI is within the above-described range, it is possible to reliably improve the yellowing resistance of the resin produced from the XDI composition. In particular, when the content ratio of the CBI is the above-described upper limit or less, it is possible to reliably improve the yellowing resistance of the resin produced from the XDI composition, and improve mechanical properties of the resin. Further, the XDI composition may contain a dichloromethylbenzyl isocyanate. In the following, the dichloromethylbenzyl isocyanate is described as a DCI. A content ratio of the DCI is, for example, 0.1 ppm or more, preferably 0.3 ppm or more, more preferably 0.6 ppm or more, more preferably 1.0 ppm or more, and for example, 60 ppm or less, preferably 50 ppm or less, more preferably 30 ppm or less, more preferably 20 ppm or less with respect to the total mass of the XDI composition. When the content ratio of the DCI is within the above-described range, it is possible to suppress yellowing and/or cloudiness of the resin produced from the XDI composition. The content ratio of the DCI can be measured in conformity with the method described in the paragraph [0376] of U.S. Pat. No. 6,373,536 in Patent Publication.

Also, the XDI composition may contain another component. Examples of the other component include dichloromethaneimino-methylbenzyl isocyanate, xylylene dichloride, and cyanobenzyl isocyanate.

The XDI composition may contain only one kind, or two or more kinds of the other components.

A content ratio of the other component is, for example, 0 ppm or more, and for example, 0.2 ppm or less, preferably 300 ppm or less with respect to the total mass of the XDI composition.

The concentration of a hydrolyzable chlorine (HC) in the XDI composition is, for example, 10 ppm or more, preferably 20 ppm or more, more preferably 30 ppm or more, and for example, 1000 ppm or less, preferably 500 ppm or less, more preferably 200 ppm or less. The concentration of the hydrolyzable chlorine (HC) is measured in conformity with the method for determining the hydrolyzable chlorine described in JIS K-1603-3 (2007).

2. Xylylene Diisocyanate Modified Composition

The above-described XDI composition is, if necessary, modified by a known method.

The xylylene diisocyanate modified composition (hereinafter, referred to as an XDI modified composition) is produced by modifying the above-described XDI composition, and contains at least one kind of functional groups of the following (a) to (i):

(a) isocyanurate group
(b) allophanate group
(c) biuret group
(d) urethane group
(e) urea group
(f) iminooxadiazinedione group
(g) uretdione group
(h) uretonimine group
(i) carbodiimide group More specifically, the XDI modified composition containing the functional group of the above-described (a) (isocyanurate group) contains a trimer of the XDI, and can be obtained, for example, by reacting the XDI composition in the presence of a known isocyanuration catalyst and subjecting the XDI to isocyanuration (for example, trimerization) of the XDI.

The XDI modified composition containing the functional group of the above-described (b) (allophanate group) contains an allophanate modified product of the XDI, and can be obtained, for example, by reacting the XDI composition with a monohydric alcohol or a dihydric alcohol, and then, further reacting the resulting product in the presence of a known allophanatization catalyst.

The XDI modified composition containing the functional group of the above-described (c) (biuret group) contains a biuret modified product of the XDI, and can be obtained, for example, by reacting the XDI composition with water or a secondary amine, and then, further reacting the resulting product in the presence of a known biuret-forming catalyst.

The XDI modified composition containing the functional group of the above-described (d) (urethane group) contains a polyol modified product of the XDI, and can be obtained, for example, by reaction of the XDI composition with a low molecular weight polyol (for example, trimethylolpropane).

The XDI modified composition containing the functional group of the above-described (e) (urea group) contains a polyamine modified product of the XDI, and can be obtained, for example, by reaction of the XDI composition with a polyamine.

The XDI modified composition containing the functional group of the above-described (f) (iminooxadiazinedione group) contains an iminooxadiazinedione modified product (asymmetric trimer) of the XDI, and can be obtained, for example, by reacting the XDI composition in the presence of a known iminooxadiazinedionization catalyst and subjecting the XDI to iminooxadiazinedionization (for example, trimerization).

The XDI modified composition containing the functional group of the above-described (g) (uretdione group) contains a uretdione modified product of the XDI, and can be obtained, for example, by reacting the XDI composition in the presence of a known uretdionization catalyst and subjecting the XDI to uretdionization (for example, dimerization).

The XDI modified composition containing the functional group of the above-described (h) (uretonimine group) contains a uretonimine modified product of the XDI, and can be obtained, for example, by reacting the XDI composition in the presence of a known carbodiimidation catalyst to form a carbodiimide group, and then, adding the XDI to the carbodiimide group.

The XDI modified composition containing the functional group of the above-described (i) (carbodiimide group) contains a carbodiimide modified product of the XDI, and can be obtained, for example, by reacting the XDI composition in the presence of a known carbodiimidation catalyst.

The XDI modified composition may contain at least one kind of functional groups of the above-described (a) to (i), or may contain two or more kinds of them. The XDI modified composition is generated by appropriately using the above-described reaction in combination.

These XDI modified compositions may be used alone or in combination of two or more.

<Function and Effect>

The above-described XDI composition contains the XDI and the above-described specific compound, and the content ratio of the above-described specific compound is the above-described upper limit or less. Further, the above-described XDI modified composition is obtained by modifying the above-described XDI composition.

Therefore, the resin produced from the above-described XDI composition and/or the above-described XDI modified composition has excellent yellowing resistance and excellent transparency.

In the above-described embodiment, an example of the specific compound includes the compound represented by the above-described general formula (1), and specific examples thereof include the formyl group-containing isocyanate represented by the above-described chemical formula (2) and the ethyl group-containing isocyanate represented by the above-described chemical formula (3). However, the specific compound is not limited to this.

When the XDI composition is measured by gas chromatography mass spectrometry under the above-described measurement conditions, the specific compound may not be included in the above-described general formula (1) as long as it is a compound having the retention time of 14.0 minutes to 14.6 minutes.

Further, as long as it is a compound included in the above-described general formula (1) and having a molecular weight of 161, the retention time of the specific compound may be outside the range of 14.0 minutes to 14.6 minutes when the XDI composition is measured by gas chromatography mass spectrometry under the above-described measurement conditions.

3. Polymerizable Composition

The XDI composition and/or the XDI modified composition described above are/is preferably used as a raw material for a resin. More specifically, the XDI composition and/or the XDI modified composition, as an isocyanate component, are/is contained in a polymerizable composition which is the raw material for the resin.

The polymerizable composition contains an isocyanate component and an active hydrogen group-containing component.

The isocyanate component contains the XDI composition and/or the XDI modified composition, and preferably consists of the XDI composition and/or the XDI modified composition.

Examples of the active hydrogen group-containing component include a polyol component, a polythiol component, and a polyamine component.

These active hydrogen group-containing components may be used alone or in combination of two or more.

Of the active hydrogen group-containing components, preferably, a polyol component and a polythiol component are used.

Examples of the polyol component include low molecular weight polyol and high molecular weight polyol.

The low molecular weight polyol is a compound having a number average molecular weight of 60 or more and below 400, preferably 300 or less and having two or more hydroxyl groups. Examples of the low molecular weight polyol include dihydric alcohol, trihydric alcohol, tetrahydric alcohol, pentahydric alcohol, hexahydric alcohol, heptahydric alcohol, and octahydric alcohol. Of the low molecular weight polyol, preferably, the dihydric alcohol and the trihydric alcohol are used.

Examples of the dihydric alcohol include ethylene glycol, propylene glycol, 1,3-propanediol, 1,4-butylene glycol, 1,3-butylene glycol, 1,5-pentanediol, 1,6-hexanediol, neopentyl glycol, alkane (7 to 22) diol, diethylene glycol, triethylene glycol, dipropylene glycol, 3-methyl-1,5-pentanediol, alkane-1,2-diol (C (carbon number, hereinafter, the same) of 17 to 20), isosorbide, 1,3- or 1,4-cyclohexanedimethanol and a mixture of these, 1,4-cyclohexanediol, hydrogenated bisphenol A, 1,4-dihydroxy-2-butene, 2,6-dimethyl-1-octene-3,8-diol, and bisphenol A.

Examples of the trihydric alcohol include glycerin and trimethylolpropane.

Further, an example of the low molecular weight polyol includes a polyalkylene oxide having a number average molecular weight of 60 or more and below 400. The polyalkylene oxide includes random and/or block copolymers of two or more kinds of alkylene oxides. The polyalkylene oxide is obtained by adding an alkylene oxide (for example, ethylene oxide, propylene oxide) using the above-described alcohol as an initiator.

The high molecular weight polyol is a compound having a number average molecular weight of 400 or more, preferably 500 or more, and for example, 10000 or less, preferably 5000 or less and having two or more hydroxyl groups.

Examples of the high molecular weight polyol include polyether polyol, polyester polyol, polycarbonate polyol, polyurethane polyol, epoxy polyol, vegetable oil polyol, polyolefin polyol, acrylic polyol, silicone polyol, fluorine polyol, and vinyl monomer-modified polyol.

These polyol components may be used alone or in combination of two or more.

The polyol component has a hydroxyl value of, for example, 5 mgKOH/g or more, preferably 10 mgKOH/g or more, and for example, 300 mgKOH/g or less, preferably 250 mgKOH/g or less. The hydroxyl value can be measured by an acetylation method or a phthalation method in conformity with the A method or the B method of JIS K1557-1.

Further, the polyol component has a number average molecular weight of, for example, 2000 or more, preferably 5000 or more, and for example, 100000 or less, preferably 50000 or less in terms of standard polystyrene by gel permeation chromatography (GPC) measurement.

Examples of the polythiol component include aliphatic polythiol compound such as methane dithiol, 1,2-ethanedithiol, 1,2,3-propanetrithiol, 1,2-cyclohexanedithiol, bis(2-mercaptoethyl)ether, tetrakis(mercaptomethyl)methane, diethylene glycolbis(2-mercaptoacetate), diethylene glycolbis(3-mercaptopropionate), ethylene glycolbis(2-mercaptoacetate), ethylene glycolbis(3-mercaptopropionate), trimethylolpropane tris(2-mercaptoacetate), trimethylolpropane tris(3-mercaptopropionate), trimethylolethane tris(2-mercaptoacetate), trimethylolethane tris(3-mercaptopropionate), pentaerythritol tetrakis(2-mercaptoacetate), pentaerythritol tetrakis(3-mercaptopropionate), bis(mercaptomethyl)sulfide, bis(mercaptomethyl)disulfide, bis(mercaptoethyl)sulfide, bis(mercaptoethyl)disulfide, bis(mercaptopropyl)sulfide, bis(mercaptomethylthio)methane, bis(2-mercaptoethylthio)methane, bis(3-mercaptopropylthio) methane, 1,2-bis(mercaptomethylthio)ethane, 1,2-bis(2-mercaptoethylthio)ethane, 1,2-bis(3-mercaptopropylthio) ethane, 1,2,3-tris(mercaptomethylthio)propane, 1,2,3-tris(2-mercaptoethylthio)propane, 1,2,3-tris(3-mercaptopropylthio)propane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, 2,5-dimercaptomethyl-1,4-dithiane, 2,5-dimercapto-1,4-dithiane, 2,5-dimercaptomethyl-2,5-dimethyl-1,4-dithiane, and esters of these thioglycolic acids and mercaptopropionic acids, hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), 2-mercaptoethyl ether bis(2-mercaptoacetate), 2-mercaptoethyl ether bis(3-mercaptopropionate), thiodiglycol acid bis(2-mercaptoethyl ester), thiodipropion acid bis(2-mercaptoethyl ester), dithiodiglycol acid bis(2-mercaptoethyl ester), dithiodipropion acid bis(2-mercaptoethyl ester), 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis (mercaptomethylthio)ethyl)-1,3-dithioethane, 3-mercaptomethyl-1,5-dimercapto-2,4-dithiapentane, tris (mercaptomethylthio)methane, tris(mercaptoethylthio) methane, and 2,5-bis(mercaptomethyl)-1,4-dithiane;

- aromatic polythiol compounds such as 1,2-dimercaptobenzene, 1,3-dimercaptobenzene, 1,4-dimethylcaptobenzene, 1,2-bis(mercaptomethyl)benzene, 1,3-bis (mercaptomethyl)benzene, 1,4-bis(mercaptomethyl) benzene, 1,2-bis(mercaptoethyl)benzene, 1,3-bis (mercaptoethyl)benzene, 1,4-bis(mercaptoethyl) benzene, 1,3,5-trimercaptobenzene, 1,3,5-tris (mercaptomethyl)benzene, 1,3,5-tris(mercaptomethyleneoxy)benzene, 1,3,5-tris(mercaptoethyleneoxy) benzene, 2,5-toluenedithiol, 3,4-toluenedithiol, 1,5-naphthalenedithiol, and 2,6-naphthalenedithiol; and
- heterocyclic polythiol compounds such as 2-methylamino-4,6-dithiol-sym-triazine, 3,4-thiophenedithiol, and bismuthiol.

These polythiol components may be used alone or in combination of two or more.

The polythiol component is preferably at least one kind selected from the group consisting of 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 4-mercaptomethyl-1,8-dimercapto-3,6-dithiaoctane, pentaerythritol tetrakis(2-mercaptoacetate), pentaerythritol tetrakis(3-mercaptopropionate), 2,5-bis(mercaptomethyl)-1,4-dithiane, bis(mercaptoethyl)sulfide, 1,1,3,3-tetrakis (mercaptomethylthio)propane, 4,6-bis(mercaptomethylthio)-1,3-dithiane, 2-(2,2-bis(mercaptomethylthio) ethyl)-1,3-dithioethane, 1,1,2,2-tetrakis(mercaptomethylthio)ethane, 3-mercaptomethyl-1,5-dimercapto-2,4-dithiapentane, tris(mercaptomethylthio)methane, ethylene glycol bis(3-mercaptopropionate), and diethylene glycol bis(3-mercaptopropionate).

<Function and Effect>

The above-described polymerizable composition contains, as an isocyanate component, the above-described XDI composition and/or the above-described XDI modified composition. Therefore, the resin produced from the above-described polymerizable composition has excellent yellowing resistance and excellent transparency.

4. Resin

By reacting the above-described isocyanate component with the above-described active hydrogen group-containing component, the resin is produced. In other words, the resin is a cured product of the polymerizable composition. The resin is preferably molded by known molding method. In other words, a molded article contains the resin.

Examples of the molded article of the resin include optical elements.

Examples of the optical element include lens, sheet, and film, and preferably, lens is used.

The lens is produced, for example, by reaction of the above-described XDI composition with the above-described polythiol component. For example, casting method may be used in the production of the lens.

Examples of the lens include transparent lens, sunglass lens, polarized lens, spectacle lens, camera lens, pick-up lens, and contact lens.

Further, the polymerizable composition may be also prepared as two-liquid curable resin raw material.

The two-liquid curable resin raw material contains A agent as curing agent and B agent as main agent.

The A agent contains, for example, the above-described XDI modified composition. The B agent contains, for example, the above-described polyol component.

Examples of the two-liquid curable resin raw material include two-liquid curable coating raw materials. Examples of the coating include paint and adhesive.

<Function and Effect>

The resin, the molded article, the optical element, the lens, and the coating described above contain the cured product of the polymerizable composition described above. Therefore, the resin, the molded article, the optical element, the lens, and the coating have excellent yellowing resistance and excellent transparency.

EXAMPLES

Next, the present invention is further described based on Examples below. The present invention is however not limited by these Examples. The specific numerical values in mixing ratio (content ratio), property value, and parameter used in the following description can be replaced with upper limit values (numerical values defined as "or less" or "below") or lower limit values (numerical values defined as "or more" or "above") of corresponding numerical values in mixing ratio (content ratio), property value, and parameter described in the above-described "DESCRIPTION OF EMBODIMENTS". All designations of "part" or "parts" and "%" mean part or parts by mass and % by mass, respectively, unless otherwise particularly specified.

<Evaluation Method>

In Examples, an evaluation method of each of the properties of a plastic lens was as follows.

<Refractive Index (Ne), Abbe Number (ve)>

By using a Pulfrich refractometer KPR-30 manufactured by Shimadzu Corporation, each of the refractive indexes (ne, nF', nC') at a wavelength of 546.1 nm (mercury e-line), a wavelength of 480.0 nm (Cd F' line), and a wavelength of 643.9 nm (Cd C' line) was determined to obtain each of the refractive index (ne) and the Abbe number (ve).

<Heat Resistance>

By using a thermomechanical analyzer TMA-60 manufactured by Shimadzu Corporation, a glass transition temperature Tg was measured by a TMA penetration method (50-g load, pin tip of 0.5 mmφ, temperature rising rate of 10° C./min) to be used as a reference of heat resistance.

<Calculation of Yellow Index Value (Y.I. Value) of Plastic Lens (Resin)>

A resin was prepared as a circular flat plate plastic lens having a thickness of 9 mm and a diameter of 75 mm, and the Y.I value was obtained using a spectrophotometer CM-5 manufactured by Konica Minolta, Inc.

The smaller the Y.I. value was, the better the hue of the plastic lens was, and the larger the Y.I. value was, the poorer the hue was.

<Loss Degree of Transparency of Plastic Lens (Resin)>

A resin was prepared as a circular flat plate plastic lens having a thickness of 9 mm and a diameter of 75 mm, and light from a light source (Luminar Ace LA-150A, manufactured by HAYASHI-LEPIC CO., LTD.) was transmitted through the flat plate lens. An image of the light transmitting through the flat plate lens was taken into an image processing device (manufactured by Ube Information Systems, Inc.), and then, the taken image was subjected to shade treatment. A degree of shading of the processed image was digitized for each pixel, an average value of the numerical value of the degree of shading of each pixel was obtained, and a loss degree of transparency of the flat plate lens was determined.

The smaller the loss degree of transparency was, the less the degree of loss of transparency of the resin (here, the flat plate lens) was (that is, excellent in transparency of the resin).

2. Preparation Example 1: Preparation of XDI

An autoclave including a pressure controller (volume of 2 $m^3$) equipped with a reflux condensing tube, a stirring wing, a thermometer, a hydrogen chloride gas introduction tube, a phosgene introduction tube, a raw material vessel, and a raw material charging pump was used as a reactor. The reactor was charged with 846 kg of an orthodichlorobenzene as an inert solvent, and the raw material vessel was charged with 136.2 kg (1.0 k mol) of an m-xylylenediamine and 621 kg of an orthodichlorobenzene (total amine concentration of 8.5% by mass).

Next, an internal pressure was adjusted to be higher than the atmospheric pressure by 0.01 MPa after the temperature in the reactor was increased to 120° C. Then, charging of a hydrogen chloride gas from the hydrogen chloride gas introduction tube into the reactor was started at a rate of 43.8 kg/hr, and at the same time, charging of the m-xylylenediamine diluted with an inert solvent from the raw material vessel was started at a rate of 379 kg/hr with the raw material charging pump, so that the entire amount thereof was charged over two hours. Thereafter, the mixture was further matured for one hour, while the hydrogen chloride gas was charged at 20 kg/hr.

Next, after a temperature of a reaction solution (hydrochloride slurry) was increased to 160° C. in the reactor, phosgene was introduced from the phosgene introduction tube at 100 kg/hr (1.0 k mol/hr) and reacted for eight hours, while the temperature thereof was maintained. After completion of the reaction, the unreacted phosgene and a hydrogen chloride gas were removed by purging nitrogen into the reactor. Then, the reaction solution was filtered to remove 0.8 kg (dry weight) of an unreacted hydrochloride. The resulting filtrate was desolvated to obtain 188.6 kg of a reaction mass having m-XDI purity of 98.10%.

Then, the obtained reaction mass was rectified to obtain m-XDI having m-XDI purity of 99.99% by mass.

3. Preparation Example 2: Preparation of Formyl Group-Containing Isocyanate

A pressure-resistant autoclave having a 500 ml scale was charged with 10 g (0.078 mol) of 1,3-dicyanobenzene (manufactured by FUJIFILM Wako Pure Chemical Corporation), 16.6 g (0.0078 mol of palladium) of a 5% by mass palladium carrying carbon catalyst (manufactured by N.E. CHEMCAT CORPORATION, NX-type 49% by mass water content), and 100 g of methanol (manufactured by FUJIFILM Wako Pure Chemical Corporation) as a reaction solvent.

Next, nitrogen was supplied to the autoclave to increase the pressure in the autoclave to 3.1 MPa (absolute pressure), and then, the nitrogen was expelled from the autoclave to reduce the pressure in the autoclave to 0.2 MPa (absolute pressure). This procedure was repeated four times to replace nitrogen in the autoclave.

Next, hydrogen was supplied to the autoclave to increase the pressure in the autoclave to 2.1 MPa (absolute pressure), and then, the hydrogen was expelled from the autoclave to reduce the pressure in the autoclave to 0.2 MPa (absolute pressure). This procedure was repeated four times to replace hydrogen in the autoclave.

Next, hydrogen was supplied to the autoclave to increase the pressure in the autoclave to 1.0 MPa (absolute pressure) using a pressure accumulator. Then, the content in the autoclave was stirred to subject the 1,3-dicyanobenzene to hydrogenation reaction, while the pressure in the autoclave was maintained.

When the hydrogen absorption of about 75% of theoretical amount was completed, the inside of the autoclave was subjected to nitrogen replacement to remove the hydrogen from the inside of the autoclave.

Next, the reaction solution was filtered through filter paper to remove the palladium carrying carbon catalyst from the reaction solution. Thereafter, the filtrate was concentrated with a rotary evaporator. Thereafter, a low boiling component was removed from the filtrate after concentration with a vacuum pump.

Thus, a composition containing 1-iminomethyl-3-(aminomethyl)benzene as a main component was obtained. The composition was hydrolyzed to obtain a composition containing 3-(aminomethyl)benzaldehyde as a main component.

Then, the composition containing 3-(aminomethyl)benzaldehyde as a main component was reacted with triphosgene in toluene to prepare a formyl group-containing isocyanate (3-(isocyanatomethyl)benzaldehyde) represented by the above-described chemical formula (2). After distilling off the toluene from the reaction solution, a formyl group-containing isocyanate was obtained by distillation under a reduced pressure.

When the obtained formyl group-containing isocyanate was analyzed under the above-described measurement conditions of the gas chromatography mass spectrometry, a peak was confirmed at the retention time of 14.0 minutes to 14.6 minutes.

4. Examples 1 to 4 and Comparative Example 1

The XDI obtained in Preparation Example 1 and the formyl group-containing isocyanate obtained in Preparation Example 2 were mixed so that a content ratio of the formyl group-containing isocyanate in the XDI composition was the value of Table 1. Thus, an XDI composition was obtained.

A content ratio of the formyl group-containing isocyanate in the XDI composition was calculated from an area ratio of an internal reference material appearing at the retention time of 12.1 minutes to the formyl group-containing isocyanate appearing at the retention time of 14.0 minutes to 14.6 minutes by adding the following internal reference material to the obtained XDI composition and analyzing it under the above-described measurement conditions of the gas chromatography mass spectrometry. The results are shown in Table 1.

Internal reference material: constant volume of 10 mL by adding 0.5 mg of a methylnaphthalene to 100 mg of an analytical sample 5. Production of Plastic Lens Each of the XDI compositions of Examples and Comparative Example (52 parts by mass), 0.01 parts by mass of a dibutyltin dichloride as a curing catalyst, 0.10 parts by mass of ZELEC UN (trade name, manufactured by Stepan, acid phosphate ester), and 1.5 parts by mass of BioSorb 583 (manufactured by SAKAI CHEMICAL INDUSTRY CO., LTD., ultraviolet absorber) were mixed and dissolved at 20° C. Then, 48 parts by mass of a polythiol component containing a 4-mercaptomethyl-1,8-dimercapto-3,6-dithiaoctane as a main component was charged and mixed to obtain a mixed uniform solution. The uniform solution was defoamed at 600 Pa for one hour, and thereafter, filtration was carried out with a 1-μm Teflon (trademark) filter to be then injected into a mold consisting of a glass mold and a tape. The mold was put into an oven, and the temperature thereof was gradually increased from 10° C. to 120° C. to be polymerized for 38 hours. After completion of the polymerization, the mold was taken out from the oven, and the mold was removed to obtain a resin. The resulting resin was furthermore annealed at 120° C. for one hour, thereby producing a plastic lens. Each of the properties was obtained based on the evaluation method of each of the properties of the above-described plastic lens. The results are shown in Table 1.

TABLE 1

| No. | | Ex. 1 | Ex. 2 | Ex. 3 | Ex. 4 | Comparative Ex. 1 |
|---|---|---|---|---|---|---|
| Content Ratio of Formyl Group-Containing Isocyanate in XDI Composition (ppm) | | 1000 | 1200 | 1500 | 1700 | 2200 |
| Optical Properties | Refractive Index ne | 1.6648 | 1.6647 | 1.6647 | 1.6646 | 1.6645 |
| | Abbe Number ve | 30.6 | 30.8 | 30.8 | 30.7 | 31.2 |
| Heat Resistance (° C.) | | 87.9 | 87.9 | 87.8 | 87.6 | 87.5 |
| Hue YI | | 5.05 | 5.06 | 5.12 | 5.20 | 5.63 |
| Loss degree of transparency | | 23 | 24 | 26 | 30 | 44 |

While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

INDUSTRIAL APPLICATION

The xylylene diisocyanate composition, the xylylene diisocyanate modified composition, the polymerizable composition, the resin, and the molded article of the present invention are used for optical elements such as lenses, sheets, and films.

The invention claimed is:

1. A xylylene diisocyanate composition comprising:

a xylylene diisocyanate;

a formyl group-containing isocyanate represented by Chemical Formula 1; and a chloromethylbenzyl isocyanate, wherein a content ratio of the formyl group-containing isocyanate is 10 ppm or more and 2000 ppm or less, and a content ratio of the chloromethylbenzyl isocyanate is 3000 ppm or less,

[Chemical Formula 1]

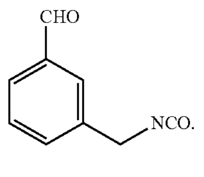

2. The xylylene diisocyanate composition according to claim 1, wherein a content ratio of the chloromethylbenzyl isocyanate is 0.2 ppm or more.

3. A xylylene diisocyanate modified composition being a modified composition obtained by modifying the xylylene diisocyanate composition according to claim 1 comprising:

at least one kind of functional groups of the following (a) to (i):

(a) isocyanurate group (b) allophanate group (c) biuret group (d) urethane group (e) urea group (f) iminooxadiazinedione group (g) uretdione group
(h) uretonimine group
(i) carbodiimide group.

4. A polymerizable composition comprising:
an isocyanate component containing the xylylene diisocyanate composition according to claim 1, and
an active hydrogen group-containing component.

5. A resin being a cured product of the polymerizable composition according to claim 4.

6. A molded article comprising:
the resin according to claim 5.

7. An optical element comprising:
the molded article according to claim 6.

8. A lens comprising:
the optical element according to claim 7.

9. A polymerizable composition comprising:
the xylylene diisocyanate modified composition according to claim 3, and
an active hydrogen group-containing component.

* * * * *